(12) United States Patent
Orenga et al.

(10) Patent No.: US 8,420,345 B2
(45) Date of Patent: Apr. 16, 2013

(54) METHOD FOR IDENTIFYING AT LEAST TWO GROUPS OF MICROORGANISMS

(75) Inventors: Sylvain Orenga, Neuville sur Ain (FR); Celine Roger-Dalbert, Chazey sur Ain (FR); Arthur James, Cockermouth (GB); John Perry, Newcastle-Upon-Tyne (GB)

(73) Assignee: Biomerieux, Marcy l'Etoile (FR)

( * ) Notice: Subject to any disclaimer, the term of this patent is extended or adjusted under 35 U.S.C. 154(b) by 212 days.

(21) Appl. No.: 12/223,025

(22) PCT Filed: Feb. 23, 2007

(86) PCT No.: PCT/FR2007/050844
§ 371 (c)(1),
(2), (4) Date: Jul. 21, 2008

(87) PCT Pub. No.: WO2007/099254
PCT Pub. Date: Sep. 7, 2007

(65) Prior Publication Data
US 2009/0017481 A1    Jan. 15, 2009

(30) Foreign Application Priority Data
Feb. 28, 2006 (FR) ..................................... 06 50693

(51) Int. Cl.
*C12Q 1/37* (2006.01)
*C12Q 1/34* (2006.01)
*C12Q 1/44* (2006.01)
*C12Q 1/42* (2006.01)

(52) U.S. Cl.
USPC ................... 435/34; 435/18; 435/19; 435/21; 435/23; 435/24

(58) Field of Classification Search .................... None
See application file for complete search history.

(56) References Cited

U.S. PATENT DOCUMENTS

| | | | |
|---|---|---|---|
| 3,453,291 A | | 7/1969 | Jackim et al. |
| 3,509,026 A | | 4/1970 | Sanders |
| 4,874,695 A | | 10/1989 | Pincus |
| 5,962,251 A | * | 10/1999 | Rambach ..................... 435/34 |
| 6,046,016 A | * | 4/2000 | Orenga ........................ 435/24 |
| 6,787,332 B2 | * | 9/2004 | Roth et al. .................... 435/34 |

FOREIGN PATENT DOCUMENTS

| | | |
|---|---|---|
| EP | 0 451 775 A1 | 10/1991 |
| EP | 1 235 928 B1 | 9/2002 |
| EP | 1 382 689 A1 | 1/2004 |
| FR | 2 659 982 A1 | 9/1991 |
| FR | 2 763 342 A1 | 11/1998 |
| WO | WO 95/04157 A1 | 2/1995 |
| WO | WO 01/30794 A1 | 5/2001 |
| WO | WO 02/44402 A1 | 6/2002 |
| WO | WO 03/035900 A1 | 5/2003 |

OTHER PUBLICATIONS

Lomolino et al. Detection of Beta-Glucosidase and Esterase Activities in Wild Yeast in a Distillery Environment; J. Inst. Brew., vol. 112, No. 2 (2006) pp. 97-100.*

James et al. Evaluation of p-Naphtholbenzein-β-D-Galactoside as a Substrate for Bacterial β-Galactosidase, Applied and Environmental Microbiology, Dec. 2000, vol. 66, No. 12, p. 5521-5523.*

Perry et al. "Evaluation of novel chromogenic substrates for the detection of bacterial β-glucosidase". *Journal of Applied Microbiology*. 2007; 102:410-5.

James et al. Note: Cyclohexenoesculetin-β-D-glucoside: a new substrate for the detection of bacterial β-glucosidase. *Journal of Applied Microbiology*. 1997; 82:532-6.

James et al. "Alizarin-β-D-galactoside: a new substrate for the detection of bacterial β-galactosidase". *Letters in Applied Microbiology*. 2000; 30:336-40.

Manafi. "New developments in chromogenic and fluorogenic culture media". *International Journal of Food Microbiology*. 2000; 60:205-18.

Mazoyer et al. "Evaluation of CPS ID2 Medium for Detection of Urinary Tract Bacterial Isolates in Specimens from a Rehabilitation Center". *Journal of Clinical Microbiology*. 1995; 33:1025-7.

Perry et al. "The application of chromogenic media in clinical microbiology". *Journal of Applied Microbiology*. 2007; 103:2046-55.

"Chromogenic medium for the enumeration of organisms in urine samples and the direct identification of *Escherichia coli*, *Enterococcus*, KES and *Proteeae*". CPS ID 2 agar (CPS2), REF 43 211/43 219. Sep. 2002; 1-4, anonymous.

Biosynth. Sales Programme. 2000; 2, anonymous.

* cited by examiner

*Primary Examiner* — Rebecca Prouty
*Assistant Examiner* — Paul Martin
(74) *Attorney, Agent, or Firm* — Oliff & Berridge, PLC

(57) ABSTRACT

The present invention relates to a method for identifying at least two groups of microorganisms expressing the same enzymatic activity, comprising the following steps:
  a) incubating said groups of microorganisms in a reaction medium comprising a first enzyme substrate and a second enzyme substrate, said first and second enzyme substrates being metabolized by the same enzymatic activity;
  b) identifying said groups of microorganisms.

3 Claims, No Drawings

METHOD FOR IDENTIFYING AT LEAST TWO GROUPS OF MICROORGANISMS

The invention relates to a method for identifying at least two groups of microorganisms expressing the same enzymatic activity. The invention also relates to a specific reaction medium and to the use thereof for identifying at least two groups of microorganisms expressing the same enzymatic activity.

For a large number of years, specific enzyme substrates have been used to determine the presence or absence of enzymatic activities characteristic of microorganisms. These enzyme substrates are generally composed of two parts, a first part specific for the enzymatic activity to be revealed, also called target part, and a second part which acts as a label, also called label part, inducing for example a specific coloration of the colony when the substrate is hydrolyzed, or the appearance of a readily detectable precipitate. Through the choice of these substrates, it is possible to characterize the nature of a microorganism, or to discriminate between various groups of microorganisms, according to whether or not there is a reaction, for example a different coloration. Thus, in the case of bacteria, *Escherichia coli* strains are commonly revealed by revealing an enzymatic activity of the osidase type, such as β-glucuronidase or β-galactosidase activity. Similarly, the *Listeria* genus can be detected by revealing a β-glucosidase activity. Mention may also be made of the detection of esterase activity for in particular revealing the *Salmonella* genus. In fact, the *Salmonella* genus possesses nonspecific esterases capable of hydrolyzing chromogenic, for example indigogenic, synthetic substrates. In the case of the detection of salmonellae, and more generally in the case of bacteria having esterase activity, the detection and/or identification of these bacteria is conventionally carried out on agar media, which allow the detection and/or identification of colonies suspected of being bacteria having esterase activity.

However, a single enzymatic activity is not always sufficient to characterize one specific group of microorganisms with respect to another group of microorganisms. For example, if it is desired to differentiate Gram-positive bacteria from Gram-negative bacteria, for instance bacteria of the KES group (*Kiebsiella, Enterobacter* and *Serratia*, Gram-negative bacteria) and those of the *Enterococcus* genus (Gram-positive bacteria), it is necessary to detect several enzymatic activities in order to increase the specificity. It is then advisable to combine several enzyme substrates in the same culture medium, which can generate a high production cost. Furthermore, in certain cases, it is not possible to spontaneously reveal different activities in the same reaction medium because the conditions for expressing the various activities are not compatible. Thus, when the chromogenic medium CPS ID 3 sold by bioMérieux is used, the bacteria of the KES group (*Klebsiella, Enterobacter* and *Serratia*, Gram-negative bacteria), like those of the *Enterococcus* genus (Gram-positive bacteria), detected by means of an osidase activity (beta-glucosidase), produce blue-green colonies: distinction between the two groups must be confirmed by means of an additional step, by a microscopic examination.

The invention proposes to solve the problems of the prior art by providing a new method particularly suitable for specifically identifying and distinguishing between various groups of microorganisms in a manner that is rapid, inexpensive and easy to implement.

Surprisingly, the inventors have demonstrated that it is possible to differentiate two groups of microorganisms expressing the same enzymatic activity, through the judicious choice of a combination of substrates specific for the enzymatic activity expressed by the two groups of microorganisms.

Before going any further with the disclosure of the invention, the following definitions are given in order to facilitate the understanding of the invention: For the purpose of the present invention, the term microorganism covers Gram-positive or Gram-negative bacteria, yeasts and, more generally, organisms that are generally single-cell organisms invisible to the naked eye that can be multiplied or manipulated in the laboratory.

By way of Gram-negative bacteria, mention may be made of bacteria of the following genera: *Pseudomonas, Escherichia, Salmonella, Shigella, Enterobacter, Klebsiella, Serratia, Proteus, Campylobacter, Haemophilus, Morganella, Vibrio, Yersinia, Acinetobacter, Branhamella, Neisseria, Burkholderia, Citrobacter, Hafnia, Edwardsiella, Aeromonas, Moraxella, Pasteurella, Providencia, Actinobacillus, Alcaligenes, Bordetella, Cedecea, Erwinia, Pantoea, Ralstonia, Stenotrophomonas, Xanthomonas* and *Legionella*.

By way of Gram-positive bacteria, mention may be made of bacteria of the following genera: *Enterococcus, Streptococcus, Staphylococcus, Bacillus, Listeria, Clostridium, Gardnerella, Kocuria, Lactococcus, Leuconostoc, Micrococcus, Mycobacteria* and *Corynebacteria*.

By way of yeasts, mention may be made of yeasts of the following genera: *Candida, Cryptococcus, Rhodotorula, Saccharomyces* and *Trichosporon*.

The term reaction medium is intended to mean a medium comprising all the elements required for the expression of a metabolism and/or for the growth of microorganisms. This reaction medium may either be used only as revealing medium, or may be used as culture and revealing medium. In the first case, the culturing of the microorganisms is carried out before inoculation, and in the second case, the reaction medium also constitutes the culture medium. This medium may contain optional other additives, for instance: peptones, one or more growth factors, carbohydrates, one or more selective agents, buffers, one or more gelling agents, etc. This reaction medium may be in the form of a liquid, or of a gel that is ready to use, i.e. ready for inoculation in a tube or a flask or on a Petri dish.

The term enzyme substrate is intended to mean any substrate that can be hydrolyzed by an enzyme to a product that allows the direct or indirect detection of a microorganism. This substrate comprises in particular a first part specific for the enzymatic activity to be revealed and a second part that acts as a label, hereinafter referred to as label part. This label part may be chromogenic, fluorogenic, luminescent, etc. As chromogenic substrate suitable for solid supports (filter, agar, electrophoresis gel), mention may in particular be made of substrates based on indoxyl and its derivatives, and substrates based on hydroxyquinoline or on esculetin and their derivatives, which allow the detection of osidase and esterase activities. By way of substrates based on indoxyl, mention may in particular be made of: 5-bromo-4-chloro-3-indolyl-N-acetyl-β-D-glucosamine, 5-bromo-3-indolyl-N-acetyl-β-D-glucosamine, 6-chloro-3-indolyl-N-acetyl-β-D-glucosamine, 5-bromo-6-chloro-3-indolyl-N-acetyl-β-D-glucosamine, 5-bromo-4-chloro-3-indolyl-N-acetyl-β-D-galactosamine, 5-bromo-4-chloro-3-indolyl-β-D-cellobioside, 5-bromo-3-indolyl-β-D-cellobioside, 6-chloro-3-indolyl-β-D-cellobioside, 5-bromo-6-chloro-3-indolyl-β-D-cellobioside, 5-bromo-4-chloro-3-indolyl-β-D-galactoside, 5-bromo-3-indolyl-β-D-galactoside, 6-chloro-3-indolyl-β-D-galactoside, 5-bromo-6-chloro-3-indolyl-β-D-galactoside, 6-bromo-3-indolyl-β-D-galactoside, 3-Indoxyl-β-D-galactoside, 5-bromo-4-chloro-3-indolyl-α-D-galactoside, 5-bromo-3-indolyl-α-D-galactoside, 6-chloro-3-indolyl-α-D-galactoside, 5-bromo-6-chloro-3-indolyl-α-D-galactoside, 5-bromo-4-chloro-3-indolyl-β-D-glucoside, 5-bromo-3-indolyl-β-D-glucoside, 6-chloro-3-indolyl-β-D-glucoside, 5-bromo-6-chloro-3-indolyl-β-D-glucoside, 5-bromo-4-chloro-3-indolyl-N-methyl-β-D-glucoside, 6-bromo-3-indolyl-β-D-glucoside, 3-indoxyl-β-D-glucoside, 5-bromo-4-chloro-3-indolyl-α-D-glucoside, 5-bromo-3-indolyl-α-D-glucoside, 6-chloro-3-indolyl-α-D-glucoside, 5-bromo-6-chloro-3-indolyl-α-D-glucoside, 5-bromo-4-chloro-3-indolyl-N-methyl-α-D-glucoside, 5-bromo-4-chloro-3-indolyl-β-D-glucuronide, 5-bromo-3-indolyl-3-D-glucuronide, 6-chloro-3-indolyl-β-D-glucuronide, 5-bromo-6-chloro-3-indolyl-β-D-glucuronide, 6-bromo-3-indolyl-β-D-glucuronide, 3-indoxyl-β-D-glucuronide, 5-bromo-4-chloro-3-indolyl-α-D-mannoside, 5-bromo-6-chloro-3-indolyl-α-D-mannoside, 6-chloro-3-indolyl-α-D-mannoside, 5-bromo-4-chloro-3-indolyl-β-D-mannoside, 5-bromo-6-chloro-3-indolyl-β-D-mannoside, 5-bromo-4-chloro-3-indolyl-β-D-riboside, 5-bromo-4-chloro-3-indolyl-β-L-fucoside, 5-bromo-4-chloro-3-indolyl-β-D-xyloside, 5-bromo-6-chloro-3-indolyl-β-D-xyloside, 5-bromo-4-chloro-3-indolylmyoinositol-1-phosphate, 5-bromo-4-chloro-3-indoxyl phosphate, 5-bromo-3-indoxyl-β-D-phosphate, 6-chloro-3-indoxyl phosphate, 5-bromo-6-chloro-3-indoxyl phosphate, 3-indoxyl phosphate, 5-bromo-4-chloro-3-indoxyl acetate, 5-bromo-3-indoxyl-β-D-acetate, 6-chloro-3-indoxyl acetate, 5-bromo-6-chloro-3-indoxyl acetate, 5-bromo-4-chloro-3-indoxyl butyrate, 5-bromo-3-indoxyl-β-D-butyrate, 6-chloro-3-indoxyl butyrate, 5-bromo-6-chloro-3-indoxyl butyrate, 5-bromo-4-chloro-3-indoxyl octanoate, 5-bromo-3-indoxyl-β-D-octanoate, 6-chloro-3-indoxyl octanoate, 5-bromo-6-chloro-3-indoxyl octanoate, 5-bromo-4-chloro-3-indoxyl nonanoate, 5-bromo-3-indoxyl-β-D-nonanoate, 6-chloro-3-indoxyl nonanoate, 5-bromo-6-chloro-3-indoxyl nonanoate, 5-bromo-4-chloro-3-indoxyl decanoate, 5-bromo-3-indoxyl-β-D-decanoate, 6-chloro-3-indoxyl decanoate, 5-bromo-4-chloro-3-indoxyl oleate, 5-bromo-4-chloro-3-indoxyl palmitate, 5-bromo-4-chloro-3-indoxyl sulfate and 5-bromo-6-chloro-3-indoxyl sulfate.

Mention may also be made of substrates derived from flavoids. The term "derived from flavoid" is intended to mean in particular 3',4'-dihydroxyflavone-4'-β-D-riboside, 3',4'-dihydroxyflavone-4'-β-D-galactoside, 3',4'-dihydroxyflavone-4'-β-D-glucoside, 3-hydroxyflavone-β-D-galactoside, 3-hydroxyflavone-β-D-glucoside or 3',4'-dihydroxyflavone-3',4'-diacetate.

Mention may also be made of substrates based on nitrophenol and nitroaniline and derivatives, for detecting osidase and esterase activities in the case of nitrophenol-based substrates, and peptidase activities in the case of nitroaniline-based substrates. Mention may also be made of substrates based on coumarin and derivatives, also for detecting osidase and esterase activities, in the case of substrates based on hydroxycoumarins, and in particular on 4-methylumbelliferone or on cyclohexenoesculetin, and peptidase activities in the case of substrates based on aminocoumarins, and in particular on 7-amino-4-methylcoumarin. Mention may also be made of substrates based on aminophenol and derivatives for detecting osidase, esterase and peptidase activities. Mention may also be made of substrates based on alizarine and derivatives for detecting osidase and esterase activities. Finally, mention may be made of substrates based on naphthol and naphthylamine and their derivatives, which make it possible to detect osidase and esterase activities by means of naphthol, and peptidase activities by means of naphthylamine.

The term "substrate based on naphthol" is intended to mean, in particular, substrates based on α-naphthol, on β-naphthol, on 6-bromo-2-naphthol, on naphthol AS BI, on naphthol AS, or on p-naphtholbenzein, as defined in patent application EP1224196 by the applicant. This may be osidase, esterase, phosphatase or sulfatase substrates. The osidase substrates are in particular N-acetyl-β-hexosaminidase, β-galactosidase, α-galacotosidase, β-glucosidase, α-glucosidase, β-glucuronidase, β-cellobiosidase or α-mannosidase substrates.

The term "substrate based on alizarine" is intended to mean, in particular, the substrates described in patent EP1235928 by the applicant, i.e. a substrate of general formula:

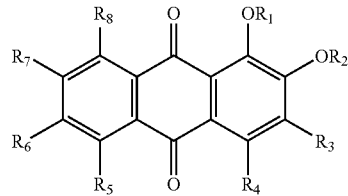

in which:
  $R_1$ is a target part or H, and $R_2$ is a target part or H, at least one of $R_1$ and $R_2$ being a target part,
  $R_3$ is H, $SO_3H$, Cl, Br, F, I, $NO_2$, $NH_2$, $NR_9R_{10}$, acylamino, aminoaryl or aminoacylamino of the NHCOX type, with X equal to alkyl, aryl and aralkyl, or an α-amino acid residue such as alanine,
  $R_4$ is H, $SO_3H$, Cl, Br, F, I, $NO_2$, $NH_2$, $NR_9R_{10}$, OH, acylamino, aminoaryl or aminoacylamino of the NHCOX type, with X equal to alkyl, aryl, aralkyl or an α-amino acid residue such as alanine,
  according to one variant, $R_3$ and $R_4$ are linked to one another so as to form a ring with at least five sides, preferably with six sides,
  $R_5$, $R_6$, $R_7$ and $R_8$ each consist of one of the following atoms or groups of atoms: H, halogen, in particular Cl or Br, OH, $SO_3H$, alkyl or alkoxy, and
  $R_9$ and $R_{10}$ consist independently of methyl, alkyl, aryl or aralkyl, or one, $R_9$ or $R_{10}$, constitutes a ring (piperidine, pyrrolidine, morpholine, etc.) and the other, $R_{10}$ or $R_9$, constitutes a hydrogen atom.

The enzyme substrate may be a natural substrate, the product of hydrolysis of which is detected directly or indirectly. As natural substrate, mention may in particular be made of tryptophan for detecting tryptophanase or deaminase activity, a cyclic amino acid (tryptophan, phenylalanine, histidine, tyrosine) for detecting deaminase activity, phosphatidyl inositol for detecting phospholipase activity, etc.

To this effect, the present invention relates to a method for identifying at least two groups of microorganisms expressing the same enzymatic activity, comprising the following steps:
  a) incubating said groups of microorganisms in a reaction medium comprising a first enzyme substrate and a second enzyme substrate, said first and second enzyme substrates being metabolized by the same enzymatic activity;
  b) identifying said groups of microorganisms.

In general, the incubation and identification steps are widely known to those skilled in the art. For example, the incubation temperature may be 37° C. As regards the incubation atmosphere, it is preferably aerobic, but it may also be anaerobic, microaerobic or under $CO_2$. The identification may be carried out with the naked eye by visualizing a change in coloration, which does not diffuse into the reaction medium, and is therefore concentrated at the colonies. In the case of the revelation of fluorescence, the fluorescence reading devices known to those skilled in the art are used.

Preferably, the invention relates to a method for identifying a first group of microorganisms and a second group of microorganisms, expressing the same enzymatic activity, comprising the following steps:
a) culturing said first and second groups of microorganisms in a reaction medium comprising a first enzyme substrate and a second enzyme substrate, said first and second enzyme substrates being metabolized by the same enzymatic activity;
b) identifying said groups of microorganisms.

Preferably, said same enzymatic activity is chosen from the following enzymatic activities: osidase, esterase and peptidase, and even more preferably, said same enzymatic activity is chosen from the following enzymatic activities: β-D-glucosidase, β-D-galactosidase, alpha-D-glucosidase, alpha-D-galactosidase, alpha-mannosidase, β-D-glucuronidase, N-acetyl-β-D-hexosaminidase, β-D-cellobiosidase, esterase, phosphatase, phospholipase, sulfatase and peptidase.

According to a preferred embodiment of the invention, said first group of microorganisms is a group of *Staphylococcus aureus* and said second group is a group of *Enterococcus faecalis*, said same enzymatic activity is an alpha-glucosidase activity, and said first and second substrates are indoxyl-based.

Preferably, the first substrate is 5-bromo-4-chloro-3-indolyl-N-methyl-alpha-glucoside and the second substrate is 6-chloro-3-indolyl-alpha-glucoside.

According to another preferred embodiment of the invention, said first and second groups of microorganisms are salmonellae of different serotypes, said same enzymatic activity is an esterase activity, and said first and second substrates are indoxyl-based.

Preferably, said first substrate is 5-bromo-4-chloro-3-indoxyl octanoate and said second substrate is 5-bromo-6-chloro-3-indoxyl octanoate.

According to another preferred embodiment of the invention, said first group of microorganisms is a group of Gram+ bacteria and said second group of microorganisms is a group of Gram− bacteria; said same enzymatic activity is a beta-glucosidase activity; said first substrate is a flavoid derivative and said second substrate is indoxyl-based.

Preferably, said first substrate is 3-hydroxyflavone-beta-glucoside, and said second substrate is 5-bromo-4-chloro-N-methyl-3-indolyl-beta-glucoside.

According to another preferred embodiment of the invention, said first group of microorganisms is a group of Gram+ bacteria and said second group of microorganisms is a group of Gram− bacteria; said same enzymatic activity is a beta-glucuronidase activity; said first substrate is naphthol-based and said second substrate is indoxyl-based.

Preferably, said first substrate is p-naphtholbenzein-beta-glucuronide and said second substrate is 6-chloro-3-indolyl-beta-glucuronide.

According to another preferred embodiment of the invention, said first group of microorganisms is a group of yeasts and said second group of microorganisms is a group of bacteria; said same enzymatic activity is a hexosaminidase activity; said first substrate is alizarine-based and said second subtrate is indoxyl-based.

Preferably, said first substrate is alizarin-N-acetyl-beta-glucosaminide and said second substrate is 5-bromo-4-chloro-3-indolyl-N-acetyl-beta-glucosaminide.

Irrespective of the embodiment of the method according to the invention, the reaction medium may also comprise at least one other substrate, preferably several, metabolized by at least one other enzymatic activity, preferably several, said other enzymatic activity preferably being chosen from a β-D-glucuronidase activity, a β-glucosidase activity, a tryptophanase activity and a deaminase activity. According to a more preferred embodiment, said other substrate is chosen from 6-chloro-3-indolyl-beta-glucuronide, 5-bromo-4-chloro-3-indolyl-N-methyl-β-D-glucoside, 3',4'-dihydroxy-4'-β-D-glucoside and tryptophan.

It is thus possible to distinguish between and identify not only a first group of Gram− bacteria and a second group of Gram+ bacteria all expressing a β-glucosidase activity, but it is also possible to identify at least a third group of bacteria expressing a β-glucuronidase activity and a fourth group of bacteria expressing a deaminase activity, and also subgroups expressing a tryptophanase activity.

The invention also relates to the use of a reaction medium comprising at least a first enzyme substrate and at least a second enzyme substrate, said first and second enzyme substrates being metabolized by the same enzymatic activity, for identifying at least two groups of microorganisms, preferably a first group of microorganisms and a second group of microorganisms, expressing the same enzymatic activity.

Preferably, the invention relates to the use of a reaction medium comprising at least a first enzyme substrate and at least a second enzyme substrate, said first and second enzyme substrates being metabolized by the same enzymatic activity, for identifying a first group of microorganisms and a second group of microorganisms, expressing the same enzymatic activity.

Preferably, said same enzymatic activity is chosen from the following enzymatic activities: osidase, esterase and peptidase, and even more preferably, said same enzymatic activity is chosen from the following enzymatic activities: β-D-glucosidase, β-D-galactosidase, alpha-D-glucosidase, alpha-D-galactosidase, alpha-mannosidase, β-D-glucuronidase, N-acetyl-β-D-hexosaminidase, β-D-cellobiosidase, esterase, phosphatase, phospholipase, sulfatase and peptidase.

According to a preferred embodiment of the invention, said first group of microorganisms is a group of *S. aureus* and said second group is a group of *E. faecalis*, said same enzymatic activity is an alpha-glucosidase activity, and said first and second substrates are indoxyl-based.

Preferably, the first substrate is 5-bromo-4-chloro-3-indolyl-N-methyl-alpha-glucoside and the second substrate is 6-chloro-3-indolyl-alpha-glucoside.

According to another preferred embodiment of the invention, said first and second groups of microorganisms are salmonellae of different serotypes, said same enzymatic activity is an esterase activity, and said first and second substrates are indoxyl-based.

Preferably, said first substrate is 5-bromo-4-chloro-3-indoxyl octanoate and said second substrate is 5-bromo-6-chloro-3-indoxyl octanoate.

According to another preferred embodiment of the invention, said first group of microorganisms is a group of Gram+ bacteria and said second group of microorganisms is a group of Gram− bacteria; said same enzymatic activity is a beta-glucosidase activity; said first substrate is a flavoid derivative and said second substrate is indoxyl-based.

Preferably, said first substrate is 3-hydroxyflavone-beta-glucoside and said second substrate is 5-bromo-4-chloro-N-methyl-3-indolyl-beta-glucoside.

According to another preferred embodiment of the invention, said first group of microorganisms is a group of Gram+ bacteria and said second group of microorganisms is a group of Gram−bacteria; said same enzymatic activity is a beta-glucuronidase activity; said first substrate is naphthol-based and said second substrate is indoxyl-based.

Preferably, said first substrate is p-naphtholbenzein-beta-glucuronide and said second substrate is 6-chloro-3-indolyl-beta-glucuronide.

According to another preferred embodiment of the invention, said first group of microorganisms is a group of yeasts and said second group of microorganisms is a group of bacteria; said same enzymatic activity is a hexosaminidase activity; said first substrate is alizarine-based and said second substrate is indoxyl-based.

Preferably, said first substrate is alizarine-N-acetyl-beta-glucosaminide and said second substrate is 5-bromo-4-chloro-3-indolyl-N-acetyl-beta-glucosaminide.

Irrespective of the mode of use of the invention, the reaction medium may also comprise at least one other substrate, preferably several, metabolized by at least one other enzymatic activity, preferably several, said other enzymatic activity preferably being chosen from a β-D-glucuronidase activity, a β-glucosidase activity, a tryptophanase activity and a deaminase activity. According to an even more preferred embodiment, said other substrate is chosen from 6-chloro-3-indolyl-beta-glucuronide, 5-bromo-4-chloro-3-indolyl-N-methyl-β-D-glucoside, 3',4'-dihydroxy-4'-β-D-glucoside and tryptophan.

It is thus possible to distinguish between and identify not only a first group of Gram−bacteria and a second group of Gram+bacteria, all expressing a β-glucosidase activity, but it is also possible to identify at least a third group of bacteria expressing a β-glucuronidase activity and a fourth group of bacteria expressing a deaminase activity, and also subgroups expressing a tryptophanase activity. Such a medium is of great use, in particular for diagnosing urinary infections.

The invention also relates to a reaction medium comprising at least a first enzyme substrate and at least a second enzyme substrate, said first and second enzyme substrates being metabolized by the same enzymatic activity.

According to a preferred embodiment of the invention, said first and second substrates are indoxyl-based; preferably, the first substrate is 5-bromo-4-chloro-3-indolyl-N-methyl-alpha-glucoside and the second substrate is 6-chloro-3-indolyl-alpha-glucoside. Such a medium is particularly suitable for identifying a group of S. aureus and a group of E. faecalis.

According to another preferred embodiment of the invention, said first and second substrates are indoxyl-based; preferably, said first substrate is 5-bromo-4-chloro-3-indoxyl octanoate and said second substrate is 5-bromo-6-chloro-3-indoxyl octanoate. Such a medium is particularly suitable for identifying two groups of salmonellae of different serotypes.

According to another preferred embodiment of the invention, said first substrate is a flavoid derivative, preferably 3-hydroxyflavone-beta-glucoside, and said second substrate is indoxyl-based, preferably 5-bromo-4-chloro-N-methyl-3-indolyl-beta-glucoside. Such a medium is particularly suitable for identifying a group of Gram+bacteria with respect to a group of Gram−bacteria.

According to another preferred embodiment of the invention, said first substrate is naphthol-based and said second substrate is indoxyl-based; preferably, said first substrate is p-naphtholbenzein-beta-glucuronide and said second substrate is 6-chloro-3-indolyl-beta-glucuronide. Such a medium is particularly suitable for identifying a group of Gram+bacteria with respect to a group of Gram−bacteria.

According to another preferred embodiment of the invention, said first substrate is alizarine-based and said second substrate is indoxyl-based; preferably, said first substrate is alizarine-N-acetyl-beta-glucosaminide and said second substrate is 5-bromo-4-chloro-3-indolyl-N-acetyl-beta-glucosaminide. Such a medium is particularly suitable for identifying a group of bacteria with respect to a group of yeasts.

Irrespective of the embodiment of the invention, the reaction medium may also comprise at least one other substrate, preferably several, metabolized by at least one other enzymatic activity, preferably several, said other enzymatic activity preferably being chosen from a β-D-glucuronidase activity, a β-glucosidase activity, a tryptophanase activity and a deaminase activity. According to an even more preferred embodiment, said other substrate is chosen from 6-chloro-3-indolyl-beta-glucuronide, 5-bromo-4-chloro-3-indolyl-N-methyl-β-D-glucoside, 3',4'-dihydroxy-4'-β-D-glucoside and tryptophan.

It is thus possible to distinguish between and identify not only a first group of Gram−bacteria and a second group of Gram+bacteria, all expressing a β-glucosidase activity, but it is also possible to identify at least a third group of bacteria expressing a β-glucuronidase activity and a fourth group of bacteria expressing a deaminase activity, and also subgroups expressing a tryptophanase activity.

The following examples are given by way of illustration and are in no way limiting in nature. They will make it possible to understand the invention more clearly.

EXAMPLE 1

Test for Determining a Differential with Respect to the Metabolism of the Same Substrate by Various Groups of Microorganisms Expressing the Same Enzymatic Activity The objective is to differentiate at least two groups of microorganisms, for example a first group and a second group, expressing the same given enzymatic activity, for example an enzymatic activity of an alpha enzyme.

The activity of each of the two groups of microorganisms is evaluated with respect to various substrates of the alpha enzyme, for example a substrate A, a substrate B and a substrate C. Each of the substrates A, B and C is added individually to a reaction medium suitable for the metabolism of said first group and said second group of microorganisms that it is desired to differentiate. A medium A comprising substrate A, a medium B comprising substrate B, a medium C comprising substrate C, etc., are thus obtained.

By way of indication, in order to distinguish between yeasts, a medium suitable for the metabolism of the yeasts may in particular be a Sabouraud medium optionally partially or totally free of glucose.

A medium suitable for the metabolism of bacteria may in particular be a tryptase soy medium or a Columbia medium.

A medium suitable for the metabolism of urinary microorganisms may in particular be a CPS ID 3 medium free of its enzyme substrates.

Of course, depending on the microorganisms to be differentiated and on the enzymatic activity studied, other reaction media may be preferred. According to the application, they may be liquid media or gel media.

Each medium is aliquoted. One or more strains of each of the groups of microorganisms to be differentiated is inoculated onto an aliquot of each medium. These cultures are then incubated under the appropriate conditions.

The hydrolysis of each of the substrates is evaluated, optionally after various incubation times, so as to determine whether there exists, between at least two substrates for the same enzymatic activity, a hydrolytic differential related to the group of microorganisms.

When such a differential is identified, a similar reaction medium supplemented with the enzyme substrates exhibiting this hydrolytic differential is produced. As previously, it is aliquoted. One or more strains of each of the groups of microorganisms to be differentiated is inoculated onto an aliquot of this medium. These cultures are then incubated under the appropriate conditions and then examined, optionally after various incubation times, in order to evaluate whether the enzymatic expression differential makes it possible to differentiate the groups of microorganisms studied. In fact, the differentiating of the groups depends not only on the hydrolytic differential between the substrates, but also on the difference between the signals produced by the hydrolysis of each of the substrates and possible interactions, in particular at the level of the enzyme substrates and/or of the signals produced.

The example developed above can be carried out in a similar manner in order to discriminate, not two groups of microorganisms, but 3, 4 or more groups of microorganisms.

EXAMPLE 2

Use of Two Indoxyl-Based Substrates for Alpha-Glucosidase, 5-Bromo-4-Chloro-3-Indolyl-N-Methyl-Alpha-Glucoside (X—N-Me-α-GLU) in Combination with 6-Chloro-3-Indolyl-Alpha-Glucoside (Rose-α-GLU [Pink-α-GLU]), for Distinguishing between the Species Staphylococcus aureus and Enterococcus Faecalis A volume of 200 ml of molten Columbia agar at 50° C. was added to various substrate compositions described in table 1 below:

TABLE 1

|  | Medium 1 | Medium 2 | Medium 3 |
| --- | --- | --- | --- |
| X-N-Me-α-GLU | 75 mg/l | — | 75 mg/l |
| Rose-α-GLU [pink-α-GLU] | — | 200 mg/l | 200 mg/l |

Three different strains of S. aureus and of E. faecalis were inoculated, using a 10 μl calibrated loop, onto each medium, using calibrated suspensions of 0.5 McFarland. All the cultures were incubated for 24 h at 37° C.

The growth and coloration results obtained at 24 h of incubation are given in table 2, in which G signifies growth, C signifies color, I signifies colorless, In signifies coloration intensity, the sign ++ signifies very good growth, the sign + signifies good growth of the strain, the sign +/− signifies moderate growth of the strain and the sign − signifies lack of growth of the strain. 1 corresponds to weak coloration intensity, 2 corresponds to moderate and 3 corresponds to strong.

TABLE 2

|  | Medium 1 | | | Medium 2 | | | Medium 3 | | |
| --- | --- | --- | --- | --- | --- | --- | --- | --- | --- |
|  | C | In | G | C | In | G | C | In | G |
| 1 S. aureus | green | 1 | + | pink | 2 | + | violet | 3 | + |
| 2 S. aureus | green | 1 | + | pink | 2 | + | violet | 1 | + |
| 3 S. aureus | green | 2 | + | pink | 2 | + | violet | 2 | + |
| 4 E. faecium | I | | + | I | | + | I | | + |
| 5 E. faecalis | green | 3 | + | pink | 1 | + | green | 3 | + |
| 6 E. faecalis | green | 3 | + | pink | 1 | + | green | 2 | + |

The results in table 2 above show that the two species tested, S. aureus and E. faecalis, exhibit different coloration intensities for each substrate. The combination of these two substrates in the same medium makes it possible to observe different colorations for each species. Thus, for the same enzymatic activity and in the presence of two substrates for this activity, it is possible to differentiate two species for which the affinity for their enzyme for each substrate is variable. In addition, if a glycopeptides, for example vancomycin or teicoplanin, is added at a suitable concentration, for example between 2 and 16 mg/l, this medium is particularly suitable for the detection of Gram-positive cocci resistant to glycopeptides, in particular those having an "acquired" resistance, such as vancomycin-resistant Staphylococcus aureus (VRSA) or vancomycin-resistant Enterococcus faecalis or E. faecium (VRE).

EXAMPLE 3

Use of Two Indoxyl-Based Substrates for Esterase, 5-Bromo-4-Chloro-3-Indoxyl Octanoate (X—C8) in Combination with 5-Bromo-6-Chloro-3-Indoxyl Octanoate (Magenta-C8), for Discriminating Salmonella Strains of Different Serotypes A volume of 200 ml of molten Columbia agar at 50° C. was added to various substrate compositions summarized in table 3 below:

TABLE 3

|  | Medium 1 | Medium 2 | Medium 3 |
| --- | --- | --- | --- |
| X-C8 | 300 mg/l | — | 300 mg/l |
| Magenta-C8 | — | 500 mg/l | 500 mg/l |

The media thus constituted were distributed into Petri dishes.

Various salmonella serotypes were inoculated, using a 10 μl calibrated loop, onto each medium, using calibrated suspensions of 0.5 McFarland. All the cultures were incubated for 24 h at 37° C.

The growth and coloration results obtained at 24 h of incubation are given in table 3, in which G signifies growth, C signifies color, I signifies colorless, In signifies coloration intensity, the sign ++ signifies very good growth, the sign + signifies good growth of the strain, the sign +/− signifies moderate growth of the strain and the sign − signifies lack of growth of the strain. 1 corresponds to a weak coloration intensity, 2 corresponds to moderate and 3 corresponds to strong.

TABLE 4

| | Medium 1 | | | Medium 2 | | | Medium 3 | | |
|---|---|---|---|---|---|---|---|---|---|
| | C | In | G | C | In | G | C | In | G |
| 1 S. enteritidis serotype Dublin | green | 1 | + | I | | + | green | 1 | + |
| 2 S. enteritidis serotype Dublin | green | 1 | + | I | | + | green | 1 | + |
| 3 S. enteritidis sterotype Enteritidis | green | 2 | + | violet | 2 | + | violet | 2 | + |
| 4 S. enteritidis sterotype Enteritidis | green | 3 | + | violet | 2 | + | violet | 3 | + |
| 5 S. enteritidis sterotype Paratyphi A | green | 1 | + | violet | 1 | + | violet | 1 | + |
| 6 S. enteritidis sterotype Typhimurium | green | 1 | + | violet | 3 | + | violet | 3 | + |

The results in table 4 show that the affinity of the esterase activity of the various salmonella sereotypes is variable according to the substrates. The Dublin serotype hydrolyzes X—C8 more specifically than Magenta-C8. Conversely, the other serotypes preferentially hydrolyze Magenta-C8, the coloration intensities being stronger for this substrate. As a result of this, a medium containing these two substrates of the same enzymatic activity makes it possible to obtain colored colonies for the various salmonella serotypes, and to separate the Dublin serotype from the other salmonella serotypes and from bacteria not expressing esterase.

EXAMPLE 4

Use of a Beta-Glucosidase Substrate, 3-Hydroxyflavone Beta-Glucoside (HF-β-GLU), or of 3',4'-Dihydroxyflavone-Beta-Glucoside (DHF-β-GLU) with an Indoxyl-Based Substrate, 5-Bromo-4-Chloro-N-Methyl-3-Indolyl-Beta-Glucoside (X—N-Me-β-GLU), for Discriminating Gram+Bacteria and Gram−Bacteria Having a Beta-Glucosidase Activity A volume of 200 ml of molten Columbia agar at 50° C. was added to various substrate compositions summarized in table 5.

TABLE 5

| | Medium 1 | Medium 2 | Medium 3 |
|---|---|---|---|
| X-N-Me-β-GLU | 75 mg/l | 75 mg/l | 75 mg/l |
| HF-β-GLU | — | — | 200 mg/l |
| DHF-β-GLU | — | 200 mg/l | — |

The media thus constituted were distributed into Petri dishes. Strains of *Enterobacter cloacae, Klebsiella pneumoniae, Serratia marcescens, Enterococcus faecium, E. faecalis, Enterococcus gallinarum, S. aureus* and *E. coli* were inoculated, using a 10 µl calibrated loop, onto each medium, using calibrated suspensions of 0.5 McFarland. All the cultures were incubated for 24 h at 37° C.

The growth and coloration results obtained at 24 h of incubation are given in table 4, in which G signifies growth, C signifies color, I signifies colorless, In signifies coloration intensity, the sign ++ signifies very good growth, the sign + signifies good growth of the strain, the sign +/− signifies moderate growth of the strain and the sign − signifies lack of growth of the strain. 1 corresponds to a weak coloration intensity, 2 corresponds to moderate, 3 corresponds to strong and 4 corresponds to very strong.

TABLE 6

| | Medium 1 | | | Medium 2 | | | Medium 3 | | |
|---|---|---|---|---|---|---|---|---|---|
| | C | In | G | C | In | G | C | In | G |
| 1 E. cloacae | green | 3 | + | green | 3 | + | green | 3 | + |
| 2 K. pneumoniae | green | 3 | + | green | 3 | + | green | 3 | + |
| 3 S. marcescens | green | 2 | + | green | 2 | + | green | 2 | + |
| 4 E. faecium | green | 4 | + | black | 4 | + | violet with metal reflections | 4 | + |
| 5 E. faecalis | green | 4 | + | black | 4 | + | Violet with metal reflections | 4 | + |
| 6 E. gallinarum | green | 4 | + | black | 4 | | Violet with metal reflections | 4 | |
| 7 S. aureus | I | | + | I | | + | I | | + |
| 8 E. coli | I | | + | I | | + | I | | + |

The results of table 6 show that the Gram-negative and beta-glucosidase-positive species preferentially hydrolyze the indoxyl-based substrate, whereas the Gram-positive and beta-glucosidase-positive species preferentially hydrolyze the flavoid-based substrates. As a result of this, it is possible to separate Gram-positive bacteria and Gram-negative bacteria having the same enzymatic activity. In fact, the differentiation of the groups depends on the hydrolytic differential between the substrates, but also on the difference between the signals produced by the hydrolysis of the substrates.

EXAMPLE 5

Use of a p-Naphtholbenzein-Beta-Glucuronide Substrate (pNB-β-GUR) with an Indoxyl-Based Substrate, 6-Chloro-3-Indolyl-Beta-Glucuronide (Rose-β-GUR) [Pink-β-GUR]) for Discriminating Gram+ Bacteria and Gram−Bacteria Having a Beta-Glucuronidase Activity A volume of 200 ml of molten Columbia agar at 50° C. was added to various substrate compositions summarized in table 7 below.

TABLE 7

| | Medium 1 | Medium 2 | Medium 3 |
|---|---|---|---|
| pNB-β-GUR | | 50 mg/l | 50 mg/l |
| Rose-β-GUR [pink-β-GUR] | 200 mg/l | — | 200 mg/l |

The media thus constituted were distributed into Petri dishes.

Various strains of microorganisms were inoculated, using a 10 µl calibrated loop, onto each medium, using calibrated suspensions of 0.5 McFarland. All the cultures were incubated for 24 h at 37° C.

The growth and coloration results obtained at 24 h of incubation are given in table 5, in which G signifies growth, C signifies color, I signifies colorless, In signifies coloration intensity, the sign ++ signifies very good growth, the sign + signifies good growth of the strain, the sign +/- signifies moderate growth of the strain and the sign – signifies lack of growth of the strain. 1 corresponds to a weak coloration intensity, 2 corresponds to moderate, 3 corresponds to strong and 4 corresponds to very strong.

TABLE 8

|   |   | Medium 1 | | | Medium 2 | | | Medium 3 | | |
|---|---|---|---|---|---|---|---|---|---|---|
|   |   | C | In | G | C | In | G | C | In | G |
| 1 | E. coli | pink | 1 | + | I | | + | pink | 1 | + |
| 2 | E. coli | pink | 3 | + | I | | + | pink | 3 | + |
| 3 | Streptococcus agalactiae | pink | 1 | + | orange | 1 | + | orange | 1 | + |
| 4 | Streptococcus agalactiae | pink | 2 | + | orange | 2 | + | orange | 2 | + |
| 5 | S. enteritidis | I | | + | I | | + | I | | + |

The results in table 8 show that the Gram-negative and beta-glucuronidase-positive species preferentially hydrolyze the indoxyl-based substrate, whereas the Gram-positive and beta-glucuronidase-positive species preferentially hydrolyze the p-naphtolbenzein-based substrates. As a result of this, it is possible to separate Gram-positive bacteria and Gram-negative bacteria having the same enzymatic activity.

EXAMPLE 6

Use of an Alizarine-Based Substrate, Alizarine-Beta-N-Acetylglucosaminide (Aliz-β-NAG), with an Indoxyl-Based Substrate, 5-Bromo-4-Chloro-3-Indolyl-Beta-N-Acetylglucosaminide (X-β-NAG), for Discriminating Bacteria and Yeasts having a Hexosaminidase Activity A volume of 200 ml of molten Columbia agar at 50° C. was added to various substrate compositions summarized in table 9.

TABLE 9

|   | Medium 1 | Medium 2 | Medium 3 |
|---|---|---|---|
| Aliz-β-NAG | 50 mg/l | — | 50 mg/l |
| X-β-NAG | — | 100 mg/l | 100 mg/l |

The media thus constituted were distributed into Petri dishes. Various strains of microorganisms were inoculated, using a 10 µl calibrated loop, onto each medium, using calibrated suspensions of 0.5 McFarland. All the cultures were incubated for 24 h at 37° C.

The growth and coloration results obtained at 24 h of incubation are given in table 6, in which G signifies growth, C signifies color, I signifies colorless, In signifies coloration intensity, the sign ++ signifies very good growth, the sign + signifies good growth of the strain, the sign +/- signifies moderate growth of the strain and the sign – signifies lack of growth of the strain. 1 corresponds to a weak coloration intensity, 2 corresponds to moderate, 3 corresponds to strong and 4 corresponds to very strong.

TABLE 10

|   |   | Medium 1 | | | Medium 2 | | | Medium 3 | | |
|---|---|---|---|---|---|---|---|---|---|---|
|   |   | C | In | G | C | In | G | C | In | G |
| 1 | Candida albicans | violet | 2 | + | green | 2 | + | blue | 3 | + |
| 2 | C. albicans | violet | 2 | + | green | 2 | + | blue | 3 | + |
| 3 | E. faecalis | violet | 3 | + | green | 1 | + | violet | 3 | + |
| 4 | Enterobacter sakasakii | violet | 3 | + | green | 2 | + | violet | 3 | + |
| 5 | E. coli | I | | + | I | | + | I | | + |

The results in table 10 show that the hexosaminidase-positive bacteria preferentially hydrolyze the alizarine-based substrate, whereas the hexosaminidase-positive yeasts preferentially hydrolyze the indoxyl-based substrates. As a result of this, it is possible to separate bacteria from yeasts having the same enzymatic activity, using two substrates for this same activity, for which the affinity of the enzyme for each group is different.

The invention claimed is:

1. A method for identifying two groups of microorganisms expressing a same enzymatic activity, comprising the following steps:
   a) incubating the two groups of microorganisms in a reaction medium comprising a first enzyme substrate and a second enzyme substrate, said first and second enzyme substrates being capable of being metabolized by the same enzymatic activity selected from the group consisting of β-D-glucosidase, β-D-galactosidase, alpha-D-glucosidase, alpha-D-galactosidase, alpha-mannosidase, β-D-glucuronidase, N-acetyl-β-D-hexosaminidase, β-D-cellobiosidase, esterase, phosphatase, phospholipase, sulfatase, and peptidase; and
   b) identifying the two groups of microorganisms based on differences between signals produced by the two groups of microorganisms from hydrolysis of the first and second enzyme substrates;
   wherein:
     it has been predetermined that each of the two groups of microorganisms exhibits different enzymatic affinities for the first and second enzyme substrates sufficiently to differentiate between the two groups of microorganisms when incubated in a reaction medium comprising a combination of the first and second enzyme substrates;
     the reaction medium further comprises at least one other substrate metabolized by at least one other enzymatic activity; and
     the microorganisms are selected from bacteria and yeasts.

2. A method for identifying two groups of microorganisms expressing a same enzymatic activity, comprising:
   a) incubating the two groups of microorganisms in a reaction medium comprising a first enzyme substrate and a second enzyme substrate, said first and second enzyme substrates being capable of being metabolized by the same enzymatic activity selected from the group consisting of β-D-glucosidase, β-D-galactosidase, alpha-D-glucosidase, alpha-D-galactosidase, alpha-mannosidase, β-D-glucuronidase, N-acetyl-β-D-hexosaminidase, β-D-cellobiosidase, esterase, phosphatase, phospholipase, sulfatase, and peptidase; and b) identifying the two groups of microorganisms based on differences between signals produced by the two groups of microorganisms from hydrolysis of the first and second enzyme substrates;

wherein:
it has been predetermined that each of the two groups of microorganisms exhibits different enzymatic affinities for the first and second enzyme substrates sufficiently to differentiate between the two groups of microorganisms when incubated in a reaction medium comprising a combination of the first and second enzyme substrates;
said two groups of microorganisms are a group of *S. aureus* and a group of *E. faecalis;*
said same enzymatic activity is an alpha-D-glucosidase activity; and
said first and second substrates are indoxyl-based.

3. The method as claimed in claim 1, wherein said other enzymatic activity is selected from the group consisting of a β-D-glucuronidase activity, a β-D-glucosidase activity, a tryptophanase activity, and a deaminase activity.

* * * * *